United States Patent [19]

Persson

[11] Patent Number: 5,484,452
[45] Date of Patent: *Jan. 16, 1996

[54] CURRENT LEAKAGE PREVENTION MECHANISM FOR USE IN A DEFIBRILLATOR CIRCUIT

[75] Inventor: Eric Persson, Minnetonka, Minn.

[73] Assignee: Surviva-Link Corporation, Minneapolis, Minn.

[*] Notice: The term of this patent shall not extend beyond the expiration date of Pat. No. 5,405,361.

[21] Appl. No.: 41,006

[22] Filed: Mar. 31, 1993

[51] Int. Cl.$^6$ ............................................. A61N 1/39
[52] U.S. Cl. ......................................... 607/5; 607/63
[58] Field of Search .............................. 607/63, 2, 5, 7, 607/8

[56] References Cited

U.S. PATENT DOCUMENTS

| | | |
|---|---|---|
| 3,706,313 | 12/1972 | Milani et al. |
| 3,886,950 | 6/1975 | Ukkestad . |
| 4,566,457 | 1/1986 | Stemple ................................. 607/5 |
| 4,823,796 | 5/1989 | Benson . |

FOREIGN PATENT DOCUMENTS 2589462  7/1964  Australia .

*Primary Examiner*—George Manuel
*Assistant Examiner*—Scott M. Getzow
*Attorney, Agent, or Firm*—Faegre & Benson

[57] ABSTRACT

A portable, automatic external defibrillator, comprising a plurality of capacitors; a capacitor charging circuit; connections from the capacitors to a patient body; and a plurality of semiconductor switches arranged to connect the capacitors to the charging circuit and to the patient body. At least one leakage shunting switch is included to prevent leakage currents from being conducted to the patient.

13 Claims, 3 Drawing Sheets

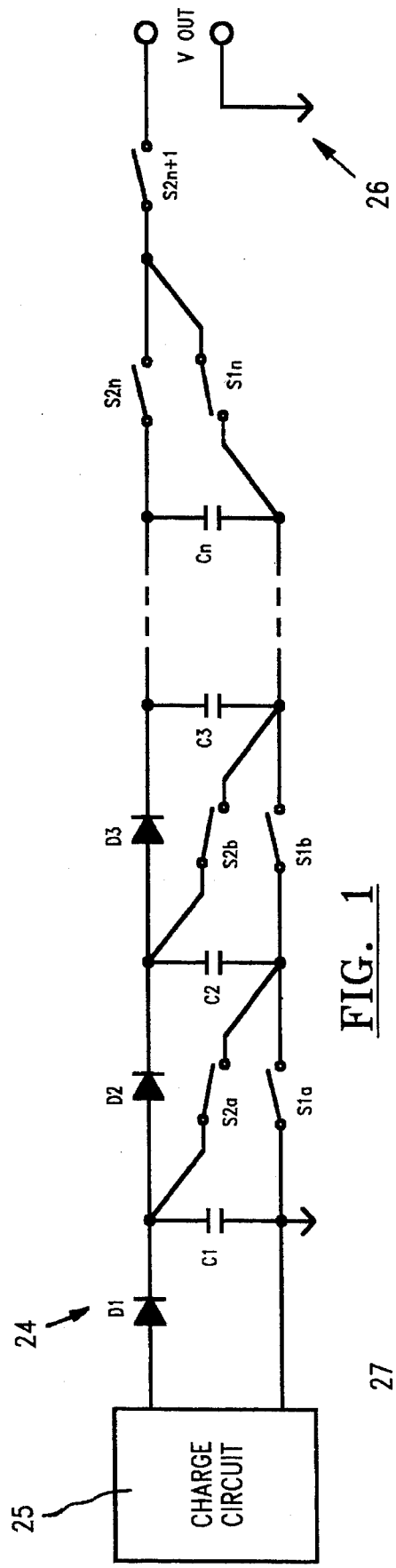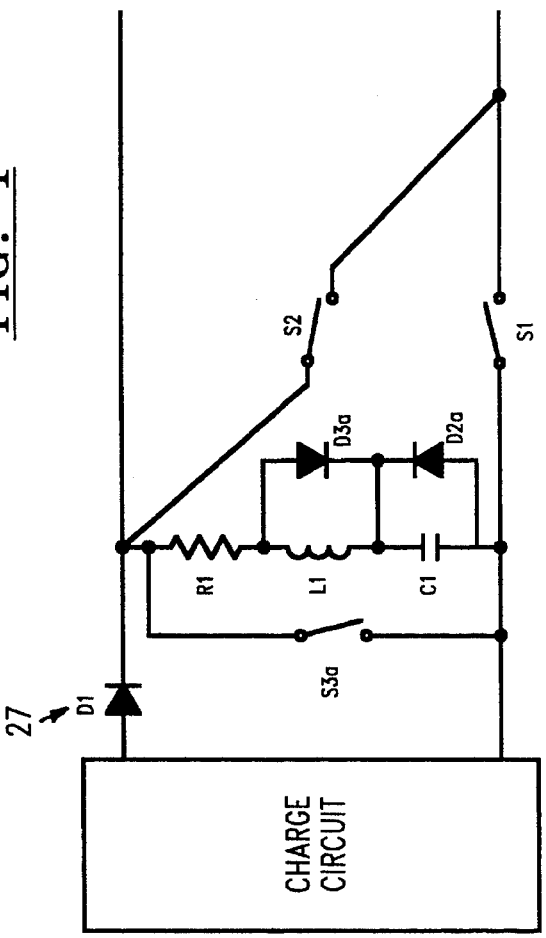

CURRENT LEAKAGE PREVENTION MECHANISM FOR USE IN A DEFIBRILLATOR CIRCUIT

BACKGROUND OF THE INVENTION

This invention relates to medical therapeutic apparatus. More particularly, this invention relates to electronic circuitry for use in an external defibrillator apparatus. The apparatus of this invention provides an improved, safer defibrillator.

The external defibrillator is a well recognized and important tool for resuscitating cardiac arrest patients. Defibrillation of the human heart is accomplished by applying an electrical waveform t o the cardiac muscle with appropriate electrodes, causing the cessation of rapid uncoordinated contractions of the heart (fibrillation) and restoration of normal beating of the heart.

In the past, defibrillators have utilized various circuitry in an attempt to minimize leakage of current to the patient during charge up. Current leakage is of particular interest in defibrillator circuitry which utilizes semiconductor components for use in switching. However, prior art circuitry has significant limitations and shortcomings. Despite the need in the art for an external defibrillator apparatus and circuitry therefor which overcomes the limitations and problems of the prior art, none insofar as is known has been proposed or developed. Accordingly, it is an object of the present invention to provide a defibrillator apparatus and circuit therefor which overcomes the limitations and shortcomings of the prior art. Particularly, it is an object of this invention to provide an improved defibrillator apparatus which is reliable, durable, and effective at delivering defibrillating charges to the body of a patient. Another object of this invention is to provide defibrillation circuitry which minimizes current leakage to a patient during charge-up. A specific object of this invention is to provide a current leakage attenuation system for circuitry which charges a plurality of capacitors in parallel and discharges them in series utilizing a plurality of semiconductor switches.

SUMMARY OF THE INVENTION

The present invention provides a defibrillator apparatus, comprising:

a) at least one capacitor;

b) means to charge the capacitor;

c) means to connect the capacitor to a patient;

d) semiconductor means to switch the capacitors between the charge means and the connection means to thereby charge and discharge the capacitor; and e) means to attenuate leakage current to a patient.

In a preferred embodiment, the invention provides an automatic external defibrillator apparatus, comprising:

a) "x" number of capacitors, where "x" is greater than 1, selectively connected in parallel with each other, each capacitor having first and second electrodes;

b) means to charge the capacitors;

c) at least two medical connection electrodes, communicatively connectible to the capacitors and for placement on the body of a patient;

d) "x–1" number of the first semiconductor switches disposed in series with each other, each between the first electrode of capacitor "n" and the first electrode of capacitor "n+1", and "n" number of second semiconductor switches disposed in series with each other, each between the second electrode of capacitor "n" and the first electrode of capacitor "n+1";

e) "x" number of diodes disposed in series with each other, each being disposed between the second electrode of capacitor "n" and the second electrode of capacitor "n+1", whereby the capacitors charge in parallel and discharge in series; and f) a redundant second semiconductor switch and a an additional first semiconductor switch arranged to shunt leakage current to a patient.

These and other benefits of this invention will become clear from the following description by reference to the drawings.

BRIEF DESCRIPTION OF THE DRAWINGS

FIG. 1 is a simplified schematic diagram of one embodiment of the defibrillator circuit of the present invention.

FIG. 2 is a schematic diagram which shows detailed structure for the embodiment shown in FIG. 1.

DESCRIPTION OF THE PREFERRED EMBODIMENT

Figure 3A:
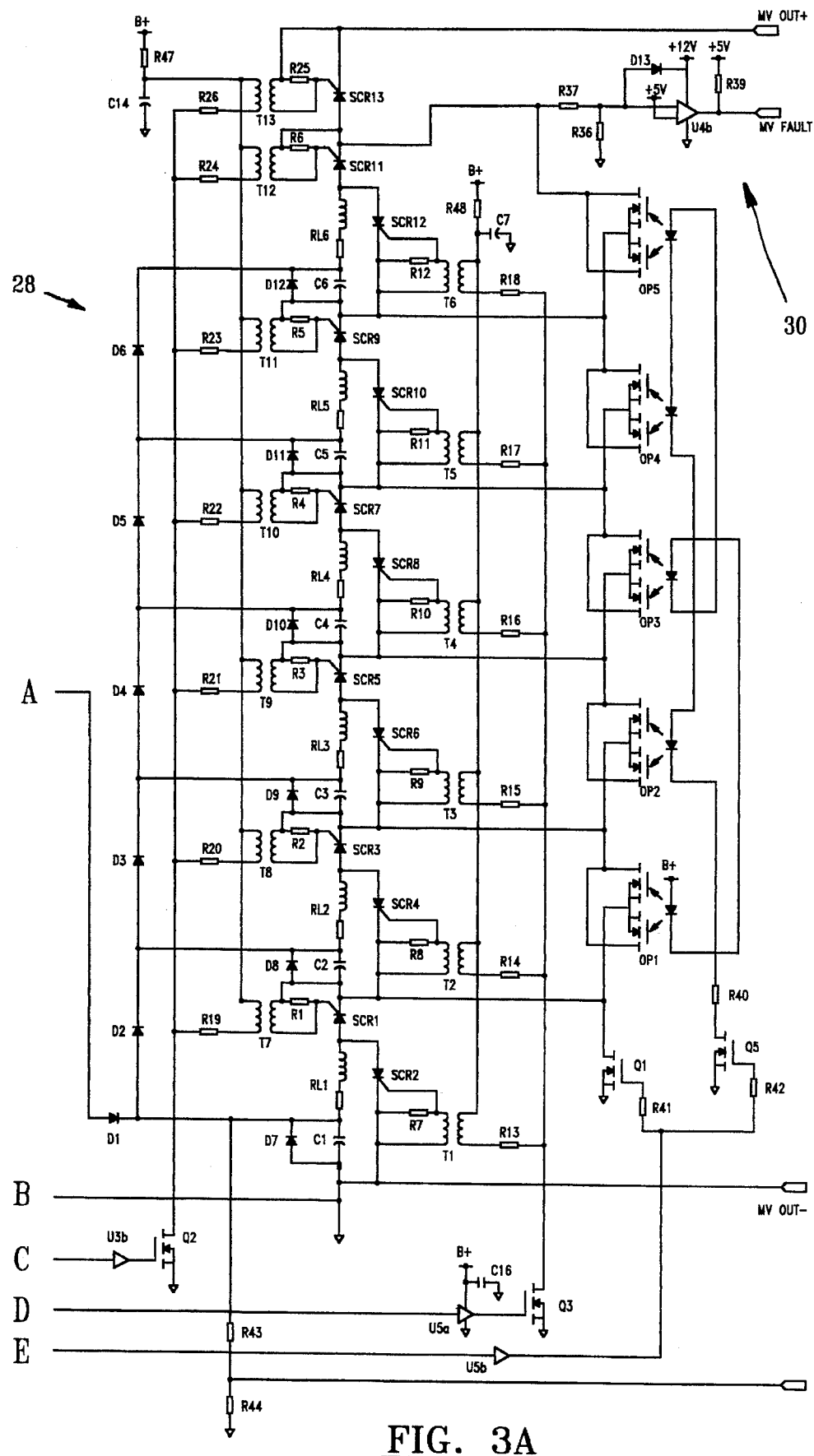
FIGS. 3A and B show a schematic diagram of the most preferred embodiment of the defibrillator circuit of this invention.
Figure 3B:
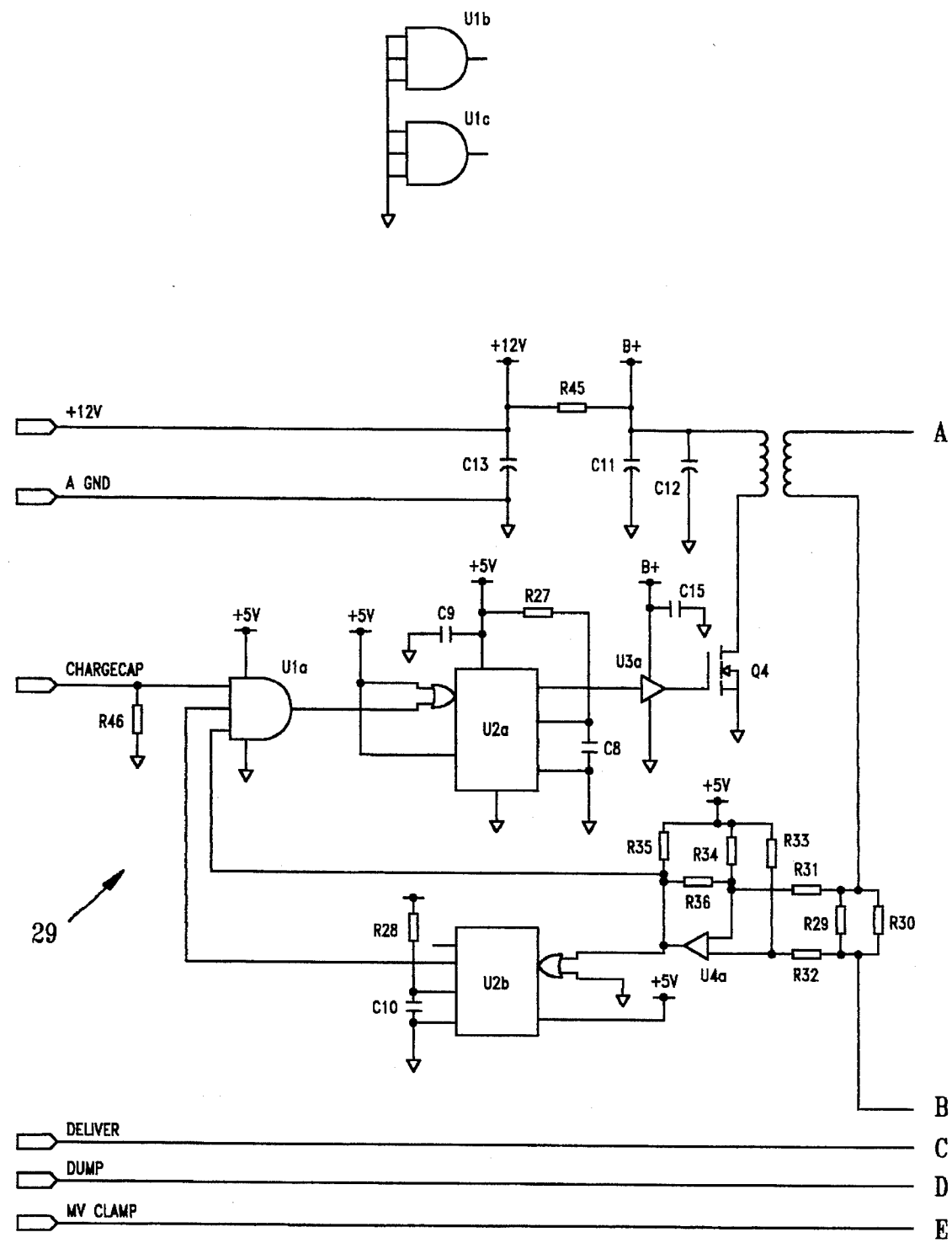

Referring to FIG. 1, a basic embodiment of circuitry 24, of the present invention, for a defibrillator is shown comprising a plurality of semiconductor switch elements S in conjunction with a charging circuit 25 and capacitors C. A plurality of 400 to 1200 V semiconductor based components, for example, thyristors are utilized to control switching from charge and discharge states in the defibrillator. The circuit 24 comprises a plurality of capacitors C(1–n), preferably six, connected to a charging circuit 25 and selectively in parallel with respect to each other. The capacitor charging circuit 25 is a current limited voltage source. Small, approximately 400 V capacitors are preferably used. The configuration of the capacitors C in parallel eliminates the voltage imbalance problem inherent in charging electrolytic capacitors in series. For convenience of reference, the electrodes or terminals of capacitors C(1–n) are designated "second" (positive) at the top end of the circuit 24, and "first" (negative) at the bottom end of the circuit 24.

Still referring to FIG. 1, the circuit 24 is constructed and arranged to allow for the charging of the capacitors C(1–n) in parallel and for discharge in series to deliver required high voltage defibrillating shocks. This is accomplished via the utilization of first semiconductor switches S1(a–n) and second S2(a–n), primarily.

Five switches S1(a–n) are disposed in series with respect to each other, each individual switch S1n being disposed between the first electrode of each individual capacitor Cn and the first electrode of its adjacent capacitor Cn+1. The first electrode of capacitor C1 is shown to be connected to ground. Six switches S2(a–n) are disposed essentially in series with each other, each individual switch S2n being disposed between the second electrode of each individual capacitor Cn and the first electrode of its adjacent capacitor Cn+1. When switches S1(a–n) are turned on the capacitors C are connected in parallel.

The last switch S2n in the series is shown to be connected between the second electrode of the last capacitor Cn in the circuit 24 and the output section 26 of the circuit 24. When switches S2(a–n) are turned on the capacitors C are now effectively in series, with the sum of their voltage appearing at Vout. Switch S2(n+1) is a redundant output switch which is turned "on at the same time as the preceding switches S2(a–n) At all times except during output, all switches S1 are "on". Therefore, any leakage currents out of switch S2n is shunted to ground through switches S1(a–n). As a result, switch S2(n+1) has essentially no voltage across it. Therefore, minimal leakage current to the patient occurs. Another advantage of this circuit configuration is that it allows for the sensing of EKG signals and for the performance of lead impedance measurements.

A plurality of diodes D(1–n) are connected in series with each other, the anodes of which are disposed towards the capacitor charging circuit 25. Diode D1 is disposed between the charging ciscuit 25 and the econd electrode of capacitor C1. The remaining diodes D2–Dn are disposed between the second electrode of each capacitor Cn and the second electrode of its adjacent capacitor Cn+1. These diodes allow for parallel charging of the capacitors C, and become reversed biased when switches S2(a–n) are turned on.

In a charge-up state, switches S2(a–n) are open and switches S1(a–n) are closed. The capacitors C1–n charge in parallel. Switches S1 can be implemented by an optocoupled transistor, such as that shown in FIG. 5 as OP1, for example. No component of this circuit 24 will see a voltage higher than the voltage present on one capacitor C. As a result, where this circuit 24 has six capacitors C and a peak circuit 24 output of approximately 2000 V, no capacitor C will see more than approximately 333 volts. This allows the use of relatively inexpensive components having the same breakdown voltage of approximately 400 V. Each capacitor Cn+1 has one (1) diode drop less voltage than its adjacent capacitor Cn. An additional benefit of this low voltage circuit configuration is that leakage currents, which are inherent in semiconductor components and on the circuit boards, for example, at high voltages, are minimized.

During discharge to a patient, switches S2(a–n+1) are closed and switches S1(a–n) are open. The capacitors C1–n thus discharge in series, delivering current to the patient's heart. Switches S2 can be implemented via a variety of semiconductor means, but a thyristor, triac or transistor are preferred for cost reasons. Triggering of these switches S2(a–n+1) is accomplished via a galvanically isolated circuit. Triggering is preferably accomplished. magnetically via gate drive transformers to simultaneously trigger switches S2. An optically coupled SCR or triac may alternatively be used.

Referring to FIG. 2, a segment 27 of a preferred circuit embodiment is shown. Current limit and rise time limit in the switches S2 is implemented by placing a resistor R1 and an inductor L1 in series with each capacitor Cn. Additionally, a parallel dump switch S3 is shown added across the network C1/L1/R1 to deliver an appropriate defibrillation waveform with a rapid drop in voltage at a predetermined time. This is particularly important when thyristors, which are difficult to turn off, are utilized in switching. A clamp diode D2(a–n) is added across each capacitor Cn to prevent that capacitor Cn from becoming reverse biased. In addition, a flyback diode D3(a–n) may be included across each inductor Ln if a power transistor, which can be turned off as well as on, is used in the circuit.

Referring to FIGS. 3A and B, the most preferred circuit embodiment 28 of this invention basically comprises a voltage converter circuit 29, six capacitors C1–6 connected in parallel with one another with respect to HV OUT "+" and "–". Seven diodes D1–7 are connected in series, each between first electrodes of the capacitors C1–6. First semiconductor switches Q1,OP1,2,3, and 4 are connected in series, each between second electrodes of adjacent capacitors C1–6. The first semiconductor switches OP1,2,3, and 4 are shown to be optocoupled transistors, and Q1 is a conventional FET. Second semiconductor switches SCR1, 3,5,7,9 and 11 are connected between the first and second electrodes of adjacent capacitors C. Second switches SCR 1,3,5,7,9 and 11 are shown to be magnetically triggered SCR's. As was previously discussed, the essential characteristic in the behavior of this circuit 28 is that the capacitors C1–6 charge in parallel via closure of first switches Q1,OP1, 2,3, and 4, and discharge in series via closure of second switches SCR1,3,5,7,9 and 11. Switch Op5 is used to shunt any leakage currents. Specifically, switch OP5 is used to shunt leakage current which may come from switch SCR 11. Since switches OP5,4,3,2,1 and Q1 all operate simultaneously, any leakage currents from switch SCR 11 will be shunted to ground, and the resulting voltage at the cathode of switch SCR 11 will be very low. Therefore, SCR 13 will have essentially zero volts across it, so that any leakage current to the patient through switch SCR 13 will be minimized.

Capacitor C1 preferably has a resistor R1 and an inductor L1 (combination RL1) disposed in series with it. The remaining capacitors C2–6 are similarly configured with RL networks to limit peak current and rise time in switches SCR1,3,5,7,9 and 11 during an output, or switches SCR2, 4,6,8,10 and 12 during a dump. Clamp diodes D7,8,9,10,11 and 12 are also shown disposed with respect to these capacitors. Finally, switches SCR2,4,6,8,10, and 12 are shown disposed in parallel across capacitor networks C1–6, respectively, to dump charge at a predetermined time in the discharge cycle. Preferably, switches SCR2,4,6,8,10 and 12 aide magnetically triggered SCR's.

SCR 13 is shown disposed at the final node anterior to HV Out(+) to prevent leakage of DC current upon capacitor charge up. SCR 13 is triggered simultaneously with SCR1, 3,5,7,9 and 11 and serves as a redundant switch to minimize leakage currents to the patient when capacitors are charged. Specifically, second switch SCR 13 is a redundant output switch which is turned "on" at the same time as the preceding second switches SCR 1,3,5,7,9 and 11. At all times except during output, all of the switches SCR 1,3,5,7,9,11 and 13 are "on". Therefore, any leakage currents out of switch SCR 11 is shunted to ground through switches Q1, and OP 1,2,3 and 4. As a result, SCR 13 has essentially no voltage across it. Therefore minimal leakage current to the patient occurs.

Circuit section 30 provide a means to clamp the full output voltage in the event of a failure of one of the switches SCR 1,3,5,7,9 or 11. Circuit section 30 is shown to be connected between switch SCR 11 and switch SCR 13 and comprises a comparator U4 which is connected to the microprocessor via line HV FAULT. The section 30 measures the voltage before switch SCR 13 to make sure it is at or near zero at all times except during discharge. If the voltage rises above this level, the circuit is caused to initiate an immediate dump by the microprocessor. For example, if a switch becomes defective, upon charge-up, the voltage before switch SCR 13 increases causing the the clamp circuit 30 to flag the microprocessor of the error. The microprocessor then initiates a shut down.

As many changes are possible to the embodiments of this invention utilizing the teachings thereof, the descriptions above, and the accompanying drawings should be interpreted in the illustrative and not the limited sense.

That which is claimed is:

1. A defibrillator apparatus, comprising:
   a) a plurality of capacitors;
   b) means to charge said capacitors;
   c) means to connect said capacitors to a patient;
   d) semiconductor means to switch said capacitors between said charge means and said connection means to thereby charge said capacitors in parallel and to discharge said capacitors in series, simultaneously, and
   e) means to limit current leakage to the patient only during charging of said capacitors.

2. The defibrillator of claim 1, wherein said charge means comprises a battery connected to a voltage converter circuit.

3. The defibrillator of claim 1, wherein said connection means comprises a pair of medical electrodes.

4. The defibrillator of claim 1, wherein said semiconductor means to switch are selected from the group consisting of thyristors, triacs and transistors.

5. The defibrillator of claim 1, wherein "x" number of said capacitors, where x is greater than 1, each having first and second electrodes are selectively connected in parallel between first and second electrodes of said charge means and said connection means, wherein said semiconductor means to switch include first switches and second switches, wherein "x−1" number of said first switches are disposed in series with each other, each between said first electrode of capacitor "n" and said first electrode of capacitor "n+1", and wherein "x" number of second switches are disposed in series with each other, each between said second electrode of capacitor "n" and said first electrode of capacitor "n+".

6. The defibrillator of claim 5, further comprising "x" number of diodes disposed in series with each other, each being disposed between said second electrode of capacitor "n" and said second electrode of capacitor "n+1".

7. The defibrillator of claim 5, wherein said means to limit current leakage to the patient comprises a redundant second semiconductor switch connected to said second switches and to said means to connect.

8. The defibrillator of claim 7, wherein said redundant second semiconductor switch is connected between second semiconductor switch "m" and one said medical connection electrode.

9. The defibrillator of claim 5, wherein said means to limit current leakage to the patient comprises an additional first semiconductor switch connected to said first switches and to said means to connect.

10. The defibrillator of claim 9, wherein said additional first semiconductor switch is connected between said first semiconductor switch "m" and said second semiconductor switch "m".

11. A low cost, portable, automatic external defibrillator apparatus, comprising:
   a) "x" number of capacitors, where "x" is greater than 1, selectively connected in parallel with each other, each capacitor having first and second electrodes;
   b) means to charge said capacitors;
   c) at least two medical connection electrodes, communicatively connectible to said capacitors and for placement on the body of a patient;
   d) "x−1" number of first semiconductor switches disposed in series with each other, each between said first electrode of capacitor "n" and said first electrode of capacitor "n+1", and "x" number of second semiconductor switches disposed in series with each other, each between said second electrode of capacitor "n" and said first electrode of capacitor "n+1;
   e) "x" number of diodes disposed in series with each other, each being disposed between said second electrode of capacitor "n" and said second electrode of capacitor "n+1", whereby said capacitors charge in parallel and discharge in series; and
   f) a redundant semiconductor switch connected to said second semiconductor switches and to one of said connection electrodes and an additional first switch connected to said first semiconductor switches and to one of said connecting electrodes.

12. A low cost, portable, automatic external defibrillator apparatus, comprising:
   a) "x" number of capacitors, where "x" is greater than 1, selectively connected in parallel with each other, each capacitor having first and second electrodes:
   b) means to charge said capacitors;
   c) at least two medical connection electrodes, communicatively connectible to said capacitors and for placement on the body of a patient;
   d) "x−1" number of first semiconductor switches disposed in series with each other, each between said first electrode of capacitor "n" and said first electrode of capacitor "n+1", and "x" number of second semiconductor switches disposed in series with each other, each between said second electrode of capacitor "n" and said first electrode of capacitor "n+1;
   e) "x" number of diodes disposed in series with each other, each being disposed between said second electrode of capacitor "n" and said second electrode of capacitor "n+1", whereby said capacitors charge in parallel and discharge in series, and
   f) a redundant semiconductor switch connected to said second semiconductor switches and to one of said connection electrodes.

13. A low cost, portable, automatic external defibrillator apparatus, comprising:
   a) "x" number of capacitors, where "x" is greater than 1, selectively connected in parallel with each other, each capacitor having first and second electrodes:
   b) means to charge said capacitors;
   c) at least two medical connection electrodes, communicatively connectible to said capacitors and for placement on the body of a patient;
   d) "x−1" number of first semiconductor switches disposed in series with each other, each between said first electrode of capacitor "n" and said first electrode of capacitor "n+1", and "x" number of second semiconductor switches disposed in series with each other, each between said second electrode of capacitor "n" and said first electrode of capacitor "n+1;
   e) "x" number of diodes disposed in series with each other, each being disposed between said second electrode of capacitor "n" and said second electrode of capacitor "n+1", whereby said capacitors charge in parallel and discharge in series, and
   f) an additional first switch connected to said first semiconductor switches and to one of said connection electrodes.

* * * * *

UNITED STATES PATENT AND TRADEMARK OFFICE
CERTIFICATE OF CORRECTION

PATENT NO. : 5,484,452
DATED : January 16, 1996
INVENTOR(S) : Eric Persson

It is certified that error appears in the above-indentified patent and that said Letters Patent is hereby corrected as shown below:

Column 5, line 31, delete "n+" and insert therefor --n+1"--.

Column 6, line 12, delete "connecting" and insert therefor --connection--.

Column 6, line 17, delete "electrodes:" and insert therefor --electrodes;--.

Column 6, line 41, delete "electrodes:" and insert therefor --electrodes;--.

Column 6, line 57, delete "series," and insert --series;--.

Signed and Sealed this

Twenty-third Day of July, 1996

Attest:

BRUCE LEHMAN

*Attesting Officer*  *Commissioner of Patents and Trademarks*